US012715864B2

(12) United States Patent
Cernaks et al.

(10) Patent No.: US 12,715,864 B2
(45) Date of Patent: Aug. 25, 2026

(54) PROCESS FOR THE SYNTHESIS OF N-BUTYLOXYCARBONYL-3-(4-IMIDAZOL-1-YLMETHYLPHENYL)-5-ISO-BUTYLTHIOPHENE-2-SULFONAMIDE

(71) Applicant: VICORE PHARMA AB, Stockholm (SE)

(72) Inventors: Dmitrijs Cernaks, Pinki (LV); Eliza Dege, Pinki (LV)

(73) Assignee: VICORE PHARMA AB, Stockholm (SE)

( * ) Notice: Subject to any disclaimer, the term of this patent is extended or adjusted under 35 U.S.C. 154(b) by 808 days.

(21) Appl. No.: 17/924,877

(22) PCT Filed: May 14, 2021

(86) PCT No.: PCT/GB2021/051172
§ 371 (c)(1),
(2) Date: Nov. 11, 2022

(87) PCT Pub. No.: WO2021/229244
PCT Pub. Date: Nov. 18, 2021

(65) Prior Publication Data

US 2023/0183223 A1 Jun. 15, 2023

(30) Foreign Application Priority Data

May 14, 2020 (GB) ..................................... 2007122

(51) Int. Cl.
*C07D 409/10* (2006.01)

(52) U.S. Cl.
CPC .................................. *C07D 409/10* (2013.01)

(58) Field of Classification Search
CPC .................................................... C07D 409/10
See application file for complete search history.

(56) References Cited

U.S. PATENT DOCUMENTS

2004/0167176 A1* 8/2004 Alterman ................ A61P 25/00 548/215

FOREIGN PATENT DOCUMENTS

| | | | |
|---|---|---|---|
| JP | 2004-533457 | A | 11/2004 |
| WO | 02/096883 | A1 | 12/2002 |
| WO | 2006/109048 | A1 | 10/2006 |
| WO | 2016/139475 | A1 | 9/2016 |

OTHER PUBLICATIONS

Wan et al., "Design, Synthesis, and Biological Evaluation of the First Selective Nonpeptide AT2 Receptor Agonist," Journal of Medicinal Chemistry 47(24):5995-6008 (2004).

Wu et al., "Selective Angiotensin II AT2 Receptor Agonists: Arylbenzylimidazole Structure-Activity Relationships," Journal of Medicinal Chemistry 49(24):7160-7168 (2006).

Mahalingam et al., "Selective Angiotensin II AT2 Receptor Agonists With Reduced CYP 450 Inhibition," Bioorganic & Medicinal Chemistry 18(12):4570-4590 (2010).

Saishin Souyaku Kagaku, (Japanese Translation of The Practice of Medicinal Chemistry, translated by NAGASE, Hiroshi), Second Volume, published by Technomics, Inc., Sep. 25, 1999, pp. 347-365.

International Search Report and Written Opinion for corresponding Application No. PCT/GB2021/051172 (mailed Jul. 23, 2021).

(Continued)

*Primary Examiner* — Rebecca L Anderson

(74) *Attorney, Agent, or Firm* — Troutman Pepper Locke LLP (Rochester)

(57) ABSTRACT

There is provided a new process for the synthesis of compounds of formula I, which are useful as angiotensin (Ang II) type 2 receptor agonists: by reacting a compound of formula II, with an excess of a compound of formula III, wherein W, Z and X have meanings given in the description; followed by reaction of the intermediate so formed with a suitable source of the counter-ion, W.

I

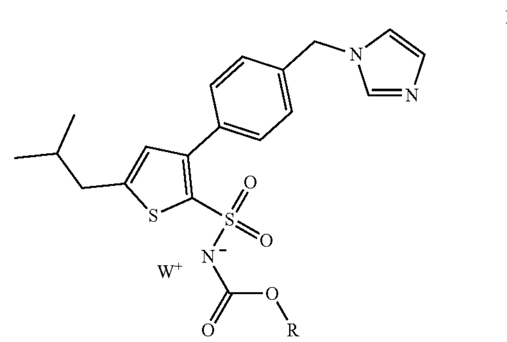

II

III

10 Claims, No Drawings

(56) References Cited

OTHER PUBLICATIONS

Wannberg et al., "A Convenient Transesterification Method for Synthesis of AT2 Receptor Ligands with Improved Stability in Human Liver Microsomes," Bioorg. Med. Chem. Lett. 28(3):519-522 (2018).

Murugaiah et al., "From the First Selective Non-Peptide AT 2 Receptor Agonist to Structurally Related Antagonists," J. Med. Chem. 55(5):2265-2278 (2012).

* cited by examiner

PROCESS FOR THE SYNTHESIS OF N-BUTYLOXYCARBONYL-3-(4-IMIDAZOL-1-YLMETHYLPHENYL)-5-ISO-BUTYLTHIOPHENE-2-SULFONAMIDE

This application is a national stage application under 35 U.S.C. § 371 of International Application No. PCT/GB2021/051172, filed May 14, 2021, which claims priority benefit to Great Britain Application No. 2007122.1, filed May 14, 2020.

FIELD OF THE INVENTION

The present invention relates to a new process that is useful in the synthesis of the angiotensin (Ang II) type 2 receptor agonist, N-butyloxycarbonyl-3-(4-imidazol-1-ylmethylphenyl)-5-iso-butylthiophene-2-sulfonamide and analogues, as well as pharmaceutically-acceptable salts thereof.

BACKGROUND OF THE INVENTION

The Renin-Angiotensin System (RAS) is a key regulator of blood pressure homeostasis. Renin, a protease, cleaves its only known substrate (angiotensinogen) to form angiotensin I (Ang I), which in turn serves as substrate to angiotensin converting enzyme (ACE) to form Ang II. The endogenous hormone Ang II is a linear octapeptide ($Asp^1$-$Arg^2$-$Val^3$-$Tyr^4$-$Ile^5$-$His^6$-$Pro^7$-$Phe^8$), and is an active component of the renin angiotensin system (RAS).

The angiotensin II type 1 (AT1) receptor is expressed in most organs, and is believed to be responsible for the majority of the pathological effects of Ang II.

Several studies in adult individuals appear to demonstrate that, in the modulation of the response following Ang II stimulation, activation of the angiotensin II type 2 (AT2) receptor has opposing effects to those mediated by the AT1 receptor.

International patent application WO 2002/096883 describes the preparation of imidazolyl, triazolyl, and tetrazolyl thiophene sulfonamides and derivatives as AT2 receptor agonists. Of the compounds described in that document (as Example 1) is N-butyloxyca rbonyl-3-(4-imidazol-1-ylmethylphenyl)-5-iso-butylthiophene-2-sulfonamide (Compound 21 or, as used hereinafter, 'C21'), which was selected for clinical development from a group of about 20 related analogues as a selective AT2 receptor agonist. C21 is now in clinical development as its sodium salt for the treatment of disorders in which treatment with an AT2 receptor agonist is believed to be beneficial, including IPF (see, for example, international patent application WO 2016/139475).

A process for the synthesis of C21 is described in Wan et al., *J. Med. Chem.* 2004, 47, p. 5995-6008. The multi-step process described therein starts with Suzuki coupling of N-tert-butylsulfonamide with 1-bromo-4-bromomethylbenzene, followed by Ullman coupling yielding the corresponding imidazole coupled intermediate. Deprotection gives the primary sulfonamide and subsequent coupling with n-butyl chloroformate yields C21 in the form of the free compound as the desired final product.

Formulative work carried out in respect of C21 free compound and salts thereof has proven extremely difficult. Part of the issue is the hitherto unreported extreme sensitivity of C21 and salts thereof to the combined presence of light and water. Attempts to provide stable solid-state formulations, even in the dry state, have produced blends with conventional excipients that are chemically unstable. As a consequence, in its first Phase I clinical trial, C21 was formulated as an aqueous solution of the sodium salt, which was frozen whilst stored and then thawed immediately prior to peroral dosing.

The compound is so unstable that, despite having worked with this active ingredient for nearly 20 years, the applicant has only recently managed to obtain a pharmaceutically-acceptable dosage form, that is one in which the active ingredient is stable when stored at ambient temperatures.

In addition to this, in attempting to develop C21 sodium salt as a commercial product, the applicant has found that synthesis in an industrial scale is extremely difficult, and at times seemed almost impossible to conduct in a commercially-viable way. In particular, the presence of elevated temperatures and/or strong bases in reaction media on such a scale has been found to contribute to the formation of undesired by-products, leading to unsatisfactory yield and unacceptable (from a pharmaceutical compliance point of view) purity of the final compound.

In addition to the undesired formation of by-products, the insolubility of C21 and/or intermediates employed in its formation was found to be a further significant problem. In particular, a sticky solid was formed, which made it very difficult to continue with the synthesis.

We have now developed a new process, as described hereinafter, that solves these problems inter alia by forming a stable intermediate that allows the formation of a stable pharmaceutically-acceptable salt of e.g. C21, preferably in a concerted manner, i.e. without the need to isolate the C21 free compound.

DISCLOSURE OF THE INVENTION

The listing or discussion of an apparently prior-published document in this specification should not necessarily be taken as an acknowledgement that the document is part of the state of the art or common general knowledge.

Unless indicated otherwise, all technical and scientific terms used herein have the same meaning as commonly understood by one of ordinary skill in the art to which this invention pertains.

The skilled person will understand that all references herein to particular aspects of the invention include references to all embodiments and combinations of one or more embodiments of that aspect of the invention. Thus, all embodiments of particular aspects of the inventions may be combined with one or more other embodiments of that aspect of the invention to form further embodiments without departing from the teaching of the invention.

According to a first aspect of the invention, there is provided a process for the preparation of a salt compound of formula I,

I

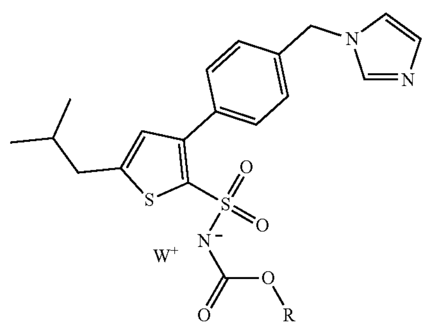

wherein R represents $C_{1-6}$ alkyl, optionally substituted by one or more halo groups, and W represents a base addition salt counter-ion, which process comprises:

(a) reaction of a compound of formula II,

II

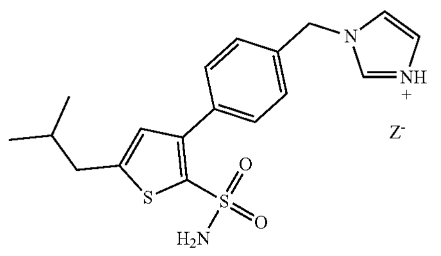

wherein Z represents an acid addition salt counter-ion, with an excess of a compound of formula III,

III

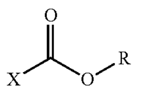

wherein X represents a suitable leaving group and R is as defined above; followed by (b) reaction of the resultant compound of formula IV,

IV

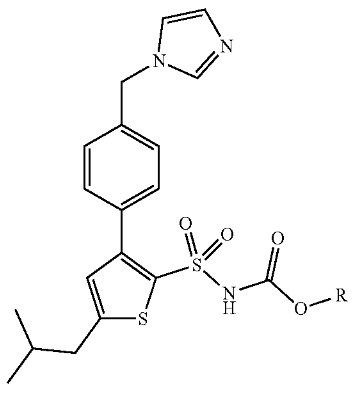

is so formed with a suitable base to provide W (i.e. the counter-ion $W^+$), as defined above, which process is hereinafter referred to as 'the process of the invention'.

$C_{1-6}$ alkyl groups (e.g. $C_{1-3}$ alkyl groups) that R may represent may be straight-chain or, when there is a sufficient number (i.e. a minimum of two or three, as appropriate) of carbon atoms, be branched-chain, and/or cyclic (so forming a $C_{3-6}$ cycloalkyl group). When there is a sufficient number (i.e. a minimum of four) of carbon atoms, such groups may also be part-cyclic (so forming a $C_{4-6}$ partial cycloalkyl group). For example, cycloalkyl groups that may be mentioned include cyclopropyl, cyclobutyl, cyclopentyl and cyclohexyl. Similarly, part-cyclic alkyl groups (which may also be referred to as 'part-cycloalkyl' groups) that may be mentioned include cyclopropylmethyl. When there is a sufficient number of carbon atoms, such groups may also be multicyclic (e.g. bicyclic or tricyclic) and/or spirocyclic.

$C_{3-6}$ alkyl groups may be unsaturated and thus incorporate a double bond or triple bond.

Particular alkyl groups that may be mentioned include straight chain (i.e. not branched and/or cyclic) alkyl groups. Preferred $C_{1-6}$ alkyl groups include, but are not limited to, propyl, such as n-propyl, 2-methylpropyl or isopropyl; ethyl; methyl and more preferably butyl, such as sec-butyl, isobutyl, tert-butyl and especially n-butyl.

Halo groups that alkyl groups may be substituted by include bromo-, chloro- or, most preferably, fluoro-groups. Halo groups may be on the same or different carbon atoms.

According to the invention, the skilled person will understand that the amount of a compound of formula III that is employed should be sufficient to allow for completion of the reaction. For example, the amount of a compound of formula III that is used in the reaction is at least about 1.5 molar equivalents relative to a compound of formula II. In particular embodiments, the amount of compound of formula III used is from about 1.75 to about 5 equivalents (e.g. from about 2 to about 3 equivalents, such as about 2.1 to about 2.5 equivalents) relative to the compound of formula II.

The process of the invention is typically conducted in the presence of one or more solvents, which may be exchanged as between separate process steps. Solvents that may be suitable for use in such reactions include polar protic solvents (e.g. water, ethanol, methanol, propanol, formic acid, hydrogen fluoride), polar aprotic solvents (e.g. dichloromethane, ethyl acetate, acetone, tetrahydrofuran, dimethylformamide, acetonitrile, dimethylsulfoxide), nonpolar solvents (e.g. pentane, heptane, hexane, cyclohexane, benzene, toluene), and/or mixtures thereof, optionally in which the reactants and/or products are soluble in, and/or in sufficient amounts for the process of the invention to proceed efficiently.

The skilled person will understand that the temperature and pressure at which the various reactions that make up the process of the invention are conducted and the duration for which the reaction conditions are maintained may be adjusted to maximise the yield and purity of the required product, e.g. the reaction may be conducted at about atmospheric pressure (i.e. about 1 atmosphere); at reduced temperature (i.e. at a temperature below about 20° C.), such as at a temperature from about 0° C. to about 15° C.; at increased temperature (i.e. at a temperature above about 20° C.), such as at a temperature from about 30° C. to about 90° C., e.g. about 35° C. to about 85° C. The appropriate duration for which the reaction conditions are maintained.

Suitable base addition salt counter-ions that W may represent include alkali metal ions (e.g. lithium, sodium, potassium), alkaline earth metal ions (e.g. magnesium and calcium) and primary, secondary or tertiary ammonium ions.

In this respect, in step (b) of the process of the invention, compounds of formula IV may be reacted with any 'suitable' base that will enable the efficient formation of the salt compound of formula I.

Suitable bases include those that allow for the formation of a corresponding alkali or alkaline earth salt. Particular bases that may be mentioned include alkali metal hydroxides (e.g. lithium hydroxide, sodium hydroxide, potassium hydroxide, rubidium hydroxide, caesium hydroxide), alkaline earth hydroxides (e.g. calcium hydroxide, magnesium hydroxide, barium hydroxide), amine bases (such as ammonia, ethylenediamine, ethanolamine, diethanolamine, triethanolamine, tromethamine), or mixtures thereof.

In preferred embodiments, W represents sodium and thus suitable bases for providing the sodium ion include sodium carbonate, sodium bicarbonate and, most preferably, sodium hydroxide.

Step (b) of the process of the invention is typically conducted in the presence of a suitable solvent system, such as a mixture of dichloromethane and methanol in a volume ratio of between about 1:1 to about 1:3, for example as described hereinafter.

The quantity of solvent, relative to the final compounds formed by way of the process of the invention should be sufficient for the reaction to proceed efficiently. For instance, a weight (in grams) of compound (e.g. of formula IV) to volume (in mL) of solvent ratio may be at least about 1:1, such as at least about 1:2, including at least about 1:3. Although the ratio may be about 1:20, particular ratios that may be mentioned are from about 1:5 to about 1:15. Higher quantities of solvent have the disadvantage that the reaction rate may decrease due to the higher dilution and additionally may have environmental/economical disadvantages.

Step (b) may be carried out for in the region of about 1 hour to 2 hours (e.g. 1.5 hours).

In step (a) of the process of the invention, that is the reaction between the compounds of formulae II and III, suitable leaving groups that X may represent may be any molecular fragment that departs a parent molecule as a result of heterolytic bond cleavage. Leaving groups may be anions or neutral molecular species. Common anionic leaving groups includes halogens, and sulfonate esters, such as mesylates and tosylates. Common neutral leaving groups include water, ammonia and methanol.

In a preferred embodiment of the invention, the leaving group X is a halogen, such as chlorine, bromine or, more preferably, iodine.

Step (a) of the process of the invention is preferably performed in the presence of a weak base. Weak bases that may be mentioned include ammonia, trimethyl ammonia, pyridines (e.g. pyridine, pyrollidinopyridine, dimethylaminopyridine), amines (e.g. hydroxylamine, methylamine, trimethylamine, tributylamine, N-ethyldiisopropylamine, di-iso-propylamine), phosphate bases (e.g. tribasic sodium phosphate), carbonate ions (e.g. potassium carbonate, sodium hydrogen carbonate, calcium carbonate), or mixtures thereof. In particular embodiments, the weak base is potassium carbonate.

Step (a) of the process of the invention is also typically conducted in the presence of a suitable solvent system, such as a mixture of water and dichloromethane in a volume ratio of between about 1.5:1 to 1:2, for example as described hereinafter.

A preferred manner of conducting step (a) of the process of the invention involves removing the counter-ion Z from a compound of formula II by reacting that salt compound with the weak base prior to addition of the excess of the compound of formula III.

The reaction in which the counter-ion is removed from a compound of a formula II, may be carried out for in the region of about 2 hours to about 4 hours (e.g. 3 hours), and the subsequent reaction between compounds of formulae II and III may be carried out for in the region of about 2 hours to about 6 hours (e.g. 4 hours).

Unless otherwise indicated, the processes described herein may be performed with or without separation (e.g. isolation and/or purification) of any stable intermediate products.

In particular, although compounds of formula II (salt forms or free compounds) may be isolated prior to reaction with a compound of formula III, for example as a solid (e.g. a crystalline solid), which may be obtained via crystallisation from a suitable solvent (such as the organic solvent used in the extraction of the product), this is not necessarily preferred, and the skilled person will understand that the counter-ion removal and coupling steps may be performed in situ.

Further, after step (a) has proceeded to completion and work-up, although the free compound of formula IV may be isolated, or stored in the solvent in which it is formed, we prefer that it is allowed to exist in that form for as little time as possible, in view of its inherent instability.

We have found in particular that conducting step (a) in the presence of the weak base allows for the formation of a compound of formula IV in situ, which can then be reacted with a source of the counter-ion, W, for example as described hereinafter.

Accordingly, it is a preferred aspect of the invention that the two steps of the process of the invention occur in a concerted manner in situ, i.e. in immediate succession in a single reaction vessel (which may also be referred to as a 'one-pot' process), with the compound of formula IV being a transient intermediate that is not isolated from the reaction mixture and not observed as a reaction product.

The reaction mixture containing the compound of formula IV may be concentrated prior to the addition of further solvents and reaction with base.

In a more particular embodiment, the process of the invention may be performed in a sealed container and, optionally, at elevated pressure (i.e. at greater than atmospheric pressure). In particular, the process may be performed in a sealed container and at elevated temperature and/or elevated pressure (e.g. wherein the container is sealed and then the contents heated to elevated temperature, thus resulting in the reaction being performed at elevated pressure).

The skilled person will understand that, in general, compounds obtained from the process of the invention may be obtained from the reaction mixture, and optionally purified, using techniques well-known in the art, such as via quenching of the reaction with an aqueous solution (such as an alkali solution, e.g. NaOH) followed by extraction from the aqueous solution using a suitable organic solvent (such as dichloromethane, methanol, ethanol or isopropyl alcohol).

In particular, compounds of formula I in the form of e.g. an alkali metal salt, such as a sodium salt, which may be formed as solids, and thus in any amorphous, crystalline and part crystalline form, may be obtained by filtration, solvent exchange to i-PrOH and/or precipitation with n-heptane, for example as described hereinafter. Compounds of formula I may also exist in the form of hydrate or solvates, all of which are included in the scope of the invention.

The process of the invention allows for the production of compounds of formula I, and the associated intermediates from which they are formed in a stable form. That is, compounds of the invention include those that are sufficiently robust to survive isolation, e.g. from a reaction mixture, to a useful degree of purity.

The process of the invention (and other process steps described herein) may be operated as a batch process or operated as a continuous (i.e. flow) process, and may be conducted on any scale.

In compounds of formula II, Z represents a suitable acid addition salt counter-ion.

Acid addition salts that may be used to provide that counter-ion include halide salts such as hydrochloride, hydrobromide and the like, sulfate salts, phosphate salts, alkaline earth salts, such as magnesium and calcium salts and alkali metal salts, such as potassium or sodium salts. More preferred salts include sulfonate salts such as toluenesulfonate salts, and alkanesulfonate salts, such as methanesulfonate, ethanesulfonate and the like. Particularly preferred salts include carboxylate salts such as formate, acetate, benzoate, oxalate, fumarate, maleate and the like.

More preferred salts include benzoate, acetate, fumarate, and most particularly, oxalate salts.

As mentioned above, we have found that certain C21 intermediates, and in particular compounds of a formula II are extremely insoluble and therefore are extremely difficult materials to work with.

We found that simply attempting to optimize the reaction conditions and parameters in the formation of compounds of formula I did not provide a solution to that problem, as the skilled person might have expected to be the case.

However, we managed to solve that problem by forming one of the above salts as hereinbefore defined, which provided a solution to the insolubility problem.

Thus, according to a further aspect of the invention, there is provided a process for the preparation of a compound of formula II, wherein the process comprises:

(i) the coupling of a compound of a formula V,

V

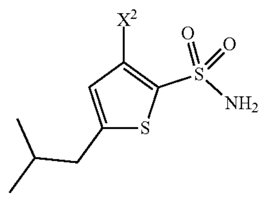

or, more preferably, a N-protected version thereof, wherein $X^2$ represents a suitable cross-coupling group, with a compound of formula VI,

VI

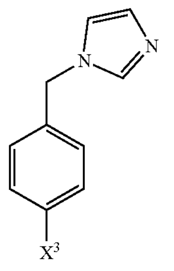

wherein $X^3$ represents a suitable cross-coupling group; followed by (ii) reaction of the intermediate so formed with a suitable acid to form a compound of a formula II as hereinbefore defined or, more preferably, a N-protected version thereof.

The above coupling reaction is preferably a Suzuki reaction, and therefore may be performed under standard Suzuki conditions, which means that one of $X^2$ and $X^3$ represents either one of the suitable Suzuki cross-coupling groups (or 'partners'), i.e. boronic acid ($—B(OH)_2$) and halo groups (as hereinbefore defined) and the other represents the other group. It is preferred that $X^2$ represents halo (such as iodo) and $X^3$ represents a boronic acid group.

Standard Suzuki conditions may be applied in this reaction, which includes the presence of an appropriate (e.g. palladium) catalyst, such as a palladium complex (e.g. palladium (II) acetate, tetrakis(triphenylphosphine)palladium (0) ($Pd(PPh_3)_4$), and tris(dibenzylideneacetone)dipalladium(0) ($Pd_2(dba)_3$), and, more preferably, [1,1'-bis(diphenylphosphino)ferrocene]dichloropalladium (II), complex with dichloromethane, or the like), a suitable base (such as potassium carbonate) and an appropriate solvent system, such as a combination of a lower alkyl alcohol (e.g. n-butanol) and water.

Formation of the salt compound of formula II may be carried out by subsequent in situ reaction of the free base intermediate with an appropriate acid that will provide the Z counter-ion as hereinbefore defined, including hydrochloric acid, hydrobromic acid, sulfuric acid or phosphoric acid; sulfonic acids, such as toluenesulfonic acid, or an alkanesulfonic acid, such as methanesulfonic acid or ethanesulfonic acid; or a carboxylic acid, such as formic acid, acetic acid, benzoic acid, oxalic acid, fumaric acid or maleic acid, and the like.

More preferred salts include acetic acid, formic acid, and, most particularly, oxalic acid.

Preferred protecting groups for compounds of formulae II (and V) include standard amino protecting groups, such as carbobenzyloxy groups, tert-butyloxycarbonyl groups, 9-fluorenylmethyloxycarbonyl groups, benzoyl groups, benzyl groups, carbamate groups and, most preferably, tert-butyl groups.

Deprotection of compounds of formula II may be carried out under routine conditions, for example using standard N-deprotecting agents known in the art, such as boron trichloride, scandium triflate, or, more preferably, hydrochloric acid or trifluoroacetic acid, and more particularly, methanesulfonic acid (e.g. in the presence of suitable carbocation scavengers, such as lithium iodide, lithium chloride, or thiophenol).

After deprotection, more acid that is the source of the acid addition counter-ion (e.g. one or more of the aforementioned acids, such as oxalic acid) may be added.

We have found that, by using the processes described above, compounds of formula II may be prepared in high purity, which avoids the need for further purification prior to subsequent reactions conducting the process of the invention.

By 'high purity' we mean greater than about 94% pure, such as greater than about 96% pure, as measured by standard techniques, such as HPLC.

Unless otherwise indicated, starting material and reagents used in processes described herein may be commercially-available and/or may themselves be synthesised from commercially-available starting materials using techniques known to those skilled in the art.

For example, compounds of formula V may be prepared by an appropriate Negishi coupling of an appropriate N-protected 5-halo-thiophene-2-sulfonamide with an appropriate source of the isobutyl group (e.g. 1M isobutylzinc bromide in THF solution), for example in the presence of catalytic amount of one of the aforementioned palladium catalysts and in the presence of a suitable base (e.g. a methyl magnesium bromide solution in Me-THF) and an appropriate solvent (e.g. THF), followed by introduction of the $X^2$ group by standard techniques (e.g. lithiation/iodination).

Compounds of formula VI may be prepared by alkylation of imidazole with an appropriate source of the benzyl moiety that is derivatised in the 4-position by $X^3$ (for example a 4-(halomethyl)phenylboronic acid) in the presence of an appropriate solvent (e.g. acetone).

Intermediates may also be isolated using standard techniques (e.g. precipitation from aqueous solution, filtration and/or chromatography).

Unless otherwise, or already, specified herein, salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared using techniques known to those skilled in the art, such as by exchanging a counter-ion of a compound of the invention in the form of a salt with another counter-ion, for example using a suitable ion exchange resin.

Compounds employed in or produced by the processes described herein (i.e. those involving the process of the invention) may exhibit tautomerism. The process of the invention therefore encompasses the use or production of such compounds in any of their tautomeric forms, or in mixtures of any such forms.

Similarly, the compounds employed in or produced by the processes described herein (i.e. those involving the process of the invention) may also contain one or more asymmetric carbon atoms and may therefore exist as enantiomers or diastereoisomers, and may exhibit optical activity. The process of the invention thus encompasses the use or production of such compounds in any of their optical or diastereoisomeric forms, or in mixtures (e.g. racemic mixtures) of any such forms.

Further, the compounds employed in or produced by the processes described herein may contain double bonds and may thus exist as E (entgegen) and Z (zusammen) geometric isomers about each individual double bond. All such isomers and mixtures thereof are included within the scope of the invention.

Wherever the word 'about' is employed herein in the context of amounts, for example absolute amounts, such as numbers, purities, weights, sizes, etc., or relative amounts (e.g. percentages, equivalents or ratios), timeframes, and parameters such as temperatures, pressure, etc., it will be appreciated that such variables are approximate and as such may vary by ±10%, for example ±5% and preferably ±2% (e.g. ±1%) from the actual numbers specified. This is the case even if such numbers are presented as percentages in the first place (for example 'about 10%' may mean±10% about the number 10, which is anything between 9% and 11%).

Processes of the invention may have the advantage that they are inter alia more efficient (e.g. higher yielding), use less energy, use less toxic reagents, produce fewer by-products and/or are cheaper to run than processes described in the prior art. In particular, processes as described herein (such as the process of the first aspect of the invention) may have the advantage that they are more suitable for use in large-scale industrial manufacture than processes described in the prior art.

In general, the processes described herein may have the advantage that they achieve higher levels of conversion and/or fewer undesired by-products (resultant of undesired side reactions) may be produced, for example, by-products that may require difficult and/or expensive purification steps. In particular, it is desirable to reduce the amount of certain impurities that may be formed, which experience has shown can be particularly difficult to separate from the desired product. The processes may thus be more economical or efficient than those described in the prior art, and provide final products that are physical and chemically stable.

The invention is illustrated, but in no way limited, by the following example. All equipment, reagents and solvents used were standard laboratory equipment, e.g. glassware, heating apparatus and HPLC apparatus.

Example 1

Sodium ((3-(4-((1H-imidazol-1-yl)methyl)phenyl)-5 isobutylthiophen 2 yl)sulfonyl) (butoxycarbonyl) amide

(a) 1-(4-(2-(N-(tert-Butyl)sulfamoyl)-5-isobutylthiophen-3-yl)benzyl)-1H-imidazol-3-ium carboxyformate oxalate salt Water (60 mL), $K_2CO_3$ (Fisher; 29.95 g), n-BuOH (Enola; 210 mL), N-(tert-butyl)-3-iodo-5-isobutylthiophene-2-sulfonamide (30.00 g; prepared by reaction of 5-bromo-N-(tert-butyl)thiophene-2-sulfonamide with 1M isobutylzinc bromide in THF solution, followed by lithiation/iodination, as described generally hereinbefore), (4-((1H-imidazol-1-yl)-methyl)phenyl)boronic acid (14.35 g; prepared by reaction of imidazole with 4-(bromomethyl)phenylboronic acid, as described generally hereinbefore) and a catalytic amount Pd(dppf)$Cl_2$·DCM (Chemtronica; 1.22 g) were added to a 1-L three-neck round bottom flask at 20° C. Argon was bubbled through the mixture and the reaction was heated to 120° C. Upon reaction completion, the reaction mixture was diluted with i-PrOAc (Acros Organics; 300 mL) and extracted with water (195 mL). The organic phase was extracted with 1% (w/w) L-cysteine aqueous solution (195 mL) to remove palladium residues, and then water (150 mL). The organic layer was concentrated and warmed to between 50° C. and 55° C., and a solution of oxalic acid (Acros Organics; 8.08 g) in EtOH (Roth; 120 mL) was added. The resultant slurry was cooled to between 0° C. and 5° C. and the product isolated by filtration. The target product was obtained in 94% yield (35.0 g) as light brown solid with a 96.5 area-% HPLC purity.

$^1$H-NMR (400 MHz, DMSO-$d_6$): 0.92 (d, 6H), 0.95 (s, 9H), 1.87 (sep, 1H), 2.68 (d, 2H), 5.37 (s, 2H), 6.92 (s, 1H), 7.28-7.33 (m, 1H), 7.38-7.44 (m, 2H), 7.48-7.51 (m, 1H), 7.55-7.60 (m, 2H), 8.56 (s, 1H), 10.77 (s, br, 1H)

$^{13}$C-NMR (100 MHz, DMSO-$d_6$): 21.87, 29.13, 29.90, 38.09, 50.34, 53.49, 120.82, 124.19, 127.82, 129.47, 129.52, 134.29, 135.86, 136.32, 137.17, 142.02, 147.11, 163.18

(b) 1-(4-(5-iso-Butyl-2-sulfamoylthiophen-3-yl)benzyl)-1H-imidazol-3-ium carboxyformate oxalate salt DCM (Telko; 270 mL), 1-(4-(2-(N-(tert-butyl)sulfamoyl)-5-isobutylthiophen-3-yl)benzyl)-1H-imidazol-3-ium carboxyformate (34.0 g; from step (a) above) and thiophenol (Acros Organics; 7.3 mL) were added to a 1-L three-neck round bottom flask. The temperature was adjusted to obtain an internal temperature of between 10 and 15° C. and methanesulfonic acid (Acros Organics; 34 mL) was added dropwise over 9 minutes whilst maintaining this internal temperature. The reaction mixture was then stirred at 20° C. for 2.5 hours. When the reaction was deemed complete, the reaction mixture was quenched by addition of water (240 mL) followed by addition of solid $K_2CO_3$ (Alfa Aesar; 51.8 g). The organic phase was separated, and the aqueous phase was extracted with DCM (270 mL), the combined organic phases were concentrated and followed by solvent exchange by co-evaporation with EtOH (3×240 mL). The resulting ethanolic solution was then concentrated and warmed up to 50 to 55° C. A solution of oxalic acid (7.04 g) in EtOH (136 mL) was added while keeping the internal temperature above 55° C. The resulting slurry was cooled to between 0° C. and 5° C. and the desired product was isolated by filtration. The filter cake was washed with EtOH (2×70 mL) and the desired product was obtained in 78% yield (23.6 g) as a beige solid with 97.4 area-% purity (HPLC).

$^{1}$H-NMR (400 MHz, DMSO-$d_6$): 0.93 (d, 6H) 1.87 (sep, 1H), 2.68 (d, 2H), 5.37 (s, 2H), 6.91 (s, 1H), 7.32-7.34 (m 1H), 7.34-7.39 (m, 2H), 7.54-7.56 (m, 1H), 7.58-7.70 (m, 4H), 8.60 (s, 1H), 11.93 (s, br, 1H)

$^{13}$C-NMR (100 MHz, DMSO-$d_6$): 21.96, 29.93, 38.08, 50.29, 120.99, 124.25, 127.50, 129.54, 129.70, 134.33, 135.97, 136.42, 137.35, 141.49, 146.14, 163.31

(c) Sodium ((3-(4-((1H-imidazol-1-yl)methyl)phenyl)-5 isobutylthiophen 2 yl) sulfonyl)(butoxycarbonyl)amide Water (315 mL) and $K_2CO_3$ (24.95 g) were added to a 1-L three-neck round bottom flask at room temperature. After stirring the mixture for 10 minutes (until complete dissolution), DCM (420 mL) and 1-(4-(5-isobutyl-2-sulfamoylthiophen-3-yl)benzyl)-1H-imidazol-3-ium carboxyformate (21.0 g; from step (b) above) were added. The temperature was adjusted to obtain an internal temperature of between 30 and 35° C. The organic layer was then extracted, water (263 mL) and $NaHCO_3$ (Fisher; 22.74 g), and then n-butyl chloroformate (Acros Organics; 13 mL) were added.

Upon completion of the reaction, the layers were separated, and IPC (HPLC) analysis of the organic phase showed full conversion to C21 free base. The organic layer was then concentrated and reacted with NaOH (Alfa Aesar; 1.98 g) in MeOH (Fisher; 210 mL). After clear-filtration, the solvent was exchanged from DCM to i-PrOH (Telko; 315 mL) via co-evaporation followed by addition of n-heptane (Fisher; 250 mL) to precipitate the product. The resulting slurry was cooled to between 0° C. and 5° C. and the product was isolated by filtration, washed on the filter with n-heptane (2×60 mL), and then dried.

The desired product was obtained in 83% yield (18.6 g) as off-white solid with purity of 99.1 area % (UPLC).

$^{1}$H-NMR (400 MHz, DMSO-$d_6$): 0.84 (t, 3H), 0.93 (d, 6H), 1.17-1.28 (m, 2H), 1.32-1.42 (m, 2H), 1.84 (sep, 1H), 2.60 (d, 2H), 3.66 (t, 2H), 5.20 (s, 2H), 6.78 (s, 1H), 6.91 (t, 1H), 7.16-7.24 (m, 3H), 7.71-7.79 (m, 3H)

$^{13}$C-NMR (100 MHz, DMSO-$d_6$): 13.71, 18.73, 22.06, 29.87, 30.92, 38.25, 49.23, 62.95, 119.58, 126.54, 128.12, 128.63, 129.53, 134.86, 136.29, 137.40, 138.21, 141.04, 143.35, 158.37.

ABBREVIATIONS

Abbreviations used herein will be well-known to those skilled in the art. For example, the following abbreviations may have meanings as indicated herein below.

C celsius
DCM dichloromethane
DMAP 4-(dimethylamino)pyridine
DMF dimethylformamide
Eq equivalent(s)
EtOH Ethanol
H hour(s)
HPLC high-performance liquid chromatography
IPC ion pair chromatography
i-PrOAc isopropyl acetate
ICP/MS inductively coupled plasma mass spectrometry
i-PrOH isopropyl alcohol
MeOH methanol
n-BuOH n-butyl alcohol
NMR nuclear magnetic resonance
PTFE polytetrafluoroethylene
THF tetrahydrofuran
UPLC ultra performance liquid chromatography

The invention claimed is:

1. A process for the preparation of a compound of formula I,

I

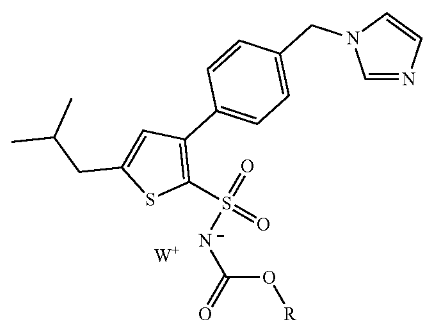

wherein R represents $C_{1-6}$ alkyl, optionally substituted by one or more halo groups, and W represents a base addition salt counter-ion, which process comprises:

(a) reaction of a compound of formula II,

II

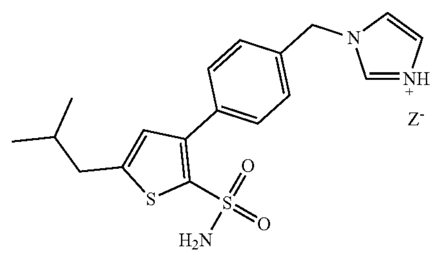

wherein Z represents an acid addition salt counter-ion, with an excess of a compound of formula III,

III

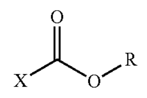

wherein X represents a suitable leaving group and R is as defined above; followed by (b) reaction of the compound of formula IV,

IV

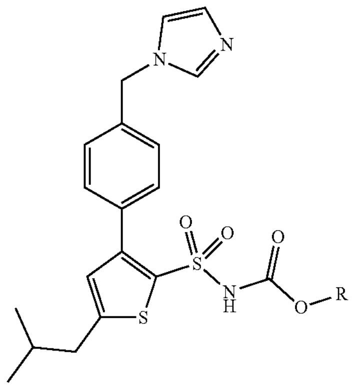

so formed with a suitable base to provide W, as defined above.

2. The process as claimed in claim 1, wherein R represents n-butyl.

3. The process as claimed in claim 1, wherein W represents Na.

4. The process as claimed in claim 1, wherein Z represents a carboxylate ion.

5. The process as claimed in claim 1, wherein Z represents an oxalate ion.

6. The process as claimed in claim 1, wherein Z is removed by a weak base.

7. The process as claimed in claim 6, wherein the weak base is selected from the group tribasic sodium phosphate, potassium carbonate, sodium hydrogen carbonate and calcium carbonate.

8. The process as claimed in claim 6, wherein the weak base is potassium carbonate.

9. The process as claimed in claim 1, wherein the ratio of the compound of formula III to the compound of formula II is between about 2:1 and about 3:1.

10. The process as claimed in claim 1, wherein the process is performed as a one-pot process and without isolation of the compound of formula IV.

* * * * *